United States Patent [19]

Francis

[11] 4,230,700

[45] Oct. 28, 1980

[54] METHODS FOR INHIBITING MOBILIZATION OF CALCIUM PHOSPHATE IN ANIMAL TISSUE

[75] Inventor: Marion D. Francis, Cincinnati, Ohio

[73] Assignee: The Procter & Gamble Company, Cincinnati, Ohio

[21] Appl. No.: 858,302

[22] Filed: Dec. 7, 1977

Related U.S. Application Data

[63] Continuation of Ser. No. 677,113, Apr. 15, 1976, abandoned, which is a continuation of Ser. No. 582,573, Jun. 2, 1975, abandoned, which is a continuation-in-part of Ser. No. 361,354, May 17, 1973, abandoned, which is a continuation-in-part of Ser. No. 260,939, Jun. 8, 1972, abandoned.

[51] Int. Cl.$^2$ .................. A61K 31/66; A61K 31/59
[52] U.S. Cl. .................. 424/204; 424/212; 424/217; 424/222; 424/236
[58] Field of Search .............. 424/204, 236, 212, 217, 424/222

[56] References Cited

U.S. PATENT DOCUMENTS

| | | | |
|---|---|---|---|
| 3,584,124 | 6/1971 | Francis | 424/204 |
| 3,584,125 | 6/1971 | Francis | 424/204 |
| 3,641,246 | 2/1972 | Francis | 424/204 |
| 3,662,066 | 5/1972 | Francis | 424/204 |
| 3,678,164 | 7/1972 | Francis | 424/204 |
| 3,683,080 | 8/1972 | Francis | 424/204 |
| 3,741,996 | 6/1973 | DeLuca et al. | 260/397.2 |

OTHER PUBLICATIONS

Goodman & Gilman—Pharmacocogical Basis of Therapeutics (1965) pp. 1687–1695.
Wilson et al.—Textbook of Organic Medicinal & Pharmaceutical Chem. (1961), pp. 783–788.
Cecil & Loeb—A Textbook of Medicine (1955), pp. 1456–1469, 9th ed.

*Primary Examiner*—Leonard Schenkman
*Attorney, Agent, or Firm*—Donald E. Hasse; Jerry J. Yetter; Richard C. Witte

[57] ABSTRACT

Compositions for inhibiting the anomalous mobilization of calcium phosphates in animal tissue comprising an effective amount of certain phosphonate compounds as herein defined in combination with Vitamin D-like antirachitic compounds, and a method for treating or preventing conditions involving hard tissue demineralization in an animal comprising concurrently administering said phosphonates and Vitamine D-like antirachitic compounds to animals.

21 Claims, No Drawings

METHODS FOR INHIBITING MOBILIZATION OF CALCIUM PHOSPHATE IN ANIMAL TISSUE

CROSS REFERENCE TO RELATED APPLICATIONS

This application is a continuation of prior application Ser. No. 677,113, filed Apr. 15, 1976 (abandoned) which is a continuation of U.S. application Ser. No. 582,573, filed June 2, 1975 (abandoned) which is a cont. in part of Ser. No. 361,354, filed May 17, 1973, (abandoned) which is a continuation-in-part of U.S. application Ser. No. 260,939, filed June 8, 1972 (abandoned).

BACKGROUND OF THE INVENTION

This invention relates to novel pharmaceutical compositions having therapeutic and prophylactic effects in disease conditions involving calcium phosphate metabolism. The invention further relates to a novel method for treating or preventing certain pathological conditions in animals.

A number of pathological conditions which can afflict warm-blooded animals are characterized by anomalous mobilization of calcium and phosphate leading to general or specific bone loss and/or excessively high calcium and phosphate levels in the fluids of the body. These conditions include osteoporosis, a disease process in which bone hard tissue is lost proportionately to the development of new hard tissue. Osteoporosis can be subclassified as post-menopausal, senile, drug-induced (e.g., adrenocorticoid as can occur in steroid therapy), disease induced (e.g., arthritic and tumor), etc., however, the manifestations are essentially the same.

Another condition involving anomalous mobilization of calcium and phosphate is Paget's disease (osteitis deformans). In this disease, dissolution of normal bone occurs which is then replaced by soft, poorly mineralized tissue such that the bone becomes deformed from pressure of weight bearing, particularly in the tibia and femur.

Until recently, no satisfactory medical treatment for disease conditions involving anomalous mobilization of calcium phosphates has been provided, although dietary Vitamin D, calcium, fluorides, estrogens, and the hormone calcitonin (thyrocaloitonin) have been suggested or tested for these conditions. More recently it has been discovered that certain phosphonate compounds as hereinafter more fully defined are effective in the treatment of such diseases. The following U.S. patents and applications, for example, are directed to the use of various phosphonates in the treatment of such disease conditions: Francis, U.S. application Ser. No. 51,355, filed June 30, 1970; U.S. Pat. No. 3,683,080, granted Aug. 8, 1972; U.S. Pat. No. 3,678,164, granted July 18, 1972; U.S. Pat. No. 3,662,066, granted May 9, 1972; U.S. Pat. No. 3,553,314, granted Jan. 5, 1971; U.S. Pat. No. 3,553,315, granted Jan. 5, 1971; U.S. Pat. No. 3,585,124, granted June 8, 1971; U.S. Pat. No. 3,584,125, granted June 8, 1971; and U.S. Pat. No. 3,641,246, granted Feb. 8, 1972.

While the compositions and methods of the foregoing patents and applications constitute an effective treatment for disease conditions such as osteoporosis, higher dosages of these compositions can cause certain adverse physiological responses. For example, higher dosages of such compounds as disodium ethane-1-hydroxy-1,1-diphosphonate can give rise to mineralization defects, i.e., lack of mineralization in mature bone (increased osteoid seams) or inhibition of mineralization of the growth cartilage and/or inhibition of primary spongiosa resorption in the epiphyseal region of bone in rapidly growing animals.

SUMMARY OF THE INVENTION

It has now been discovered that the therapeutic effectiveness of the phosphonate compounds can be enhanced to a degree that lower dosage levels can be used, thereby avoiding adverse responses, through the conjoint administration of Vitamin D-like antirachitic compounds (i.e., Vitamin D-active antirachitic compounds including Vitamin D and its precursors, analogs and metabolites) therewith. It is therefore an object of this invention to provide improved compositions and methods for treating disease conditions involving anomalous mobilization of calcium phosphate in animal tissue. It is a further object of this invention to provide improved compositions in dosage unit form containing active phosphonate compounds in combination with Vitamin D-active antirachitic compounds.

DETAILED DESCRIPTION OF THE INVENTION

In its composition aspect, the present invention is directed to a composition adapted to systemic administration to an animal comprising (1) an effective but non-toxic amount of a phosphonate selected from the group consisting of:

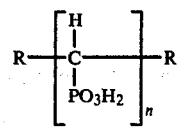

wherein each R is hydrogen or $CH_2OH$ and n is an integer of from 3 to 10;

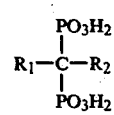

wherein $R_1$ is hydrogen, alkyl containing from 1 to about 20 carbon atoms, alkenyl containing from 2 to about 20 carbon atoms, aryl (e.g., phenyl, naphthyl), phenylethenyl, benzyl, halogen (e.g., chlorine, bromine and fluorine) hydroxyl, amino, substituted amino (e.g., dimethylamino, diethylamino, N-hydroxy-N-ethylamino, acetylamino), $-CH_2COOH$, $-CH_2PO_3H_2$, $CH(PO_3H_2)(OH)$, or $-[CH_2C(PO_3H_2)_2]_nH$ wherein n is 1 to 15, $R_2$ is hydrogen, lower alkyl (e.g., methyl, ethyl, propyl and butyl), amino, benzyl, halogen (e.g., chlorine bromine, and fluorine), hydroxyl, $-CH_2COOH$, $-CH_2PO_3H_2$, or $-CH_2CH_2PO_3H_2$;

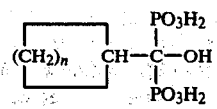

wherein n is an integer of from 3 to 9;

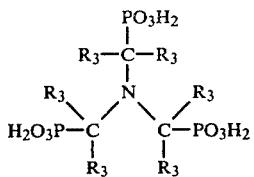

wherein each $R_3$ is hydrogen or lower alkyl (e.g., methyl, ethyl, propyl and butyl);

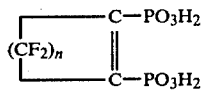

wherein n is an integer of from 2 to 4;

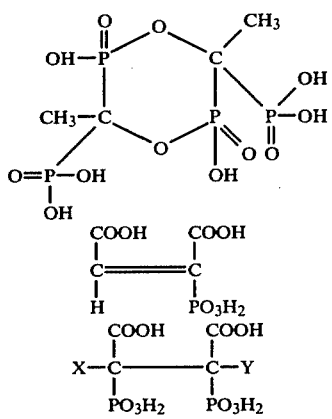

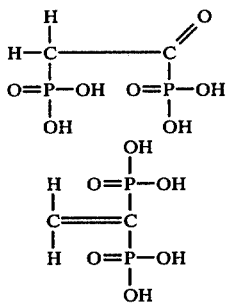

wherein X and Y are each hydrogen or hydroxy;

$$\begin{array}{c} H \\ | \\ H-C \\ | \\ O=P-OH \\ | \\ OH \end{array} \begin{array}{c} O \\ \parallel \\ C \\ | \\ O=P-OH \\ | \\ OH \end{array} \quad IX.$$

$$\begin{array}{c} \quad\quad OH \\ H \quad O=P-OH \\ | \quad\quad | \\ C===C \\ | \quad\quad | \\ H \quad O=P-OH \\ \quad\quad | \\ \quad\quad OH \end{array} \quad X.$$

and the pharmaceutically acceptable salts of each of the foregoing acids, e.g., alkali metal (sodium and potassium), alkaline earth metal (calcium and magnesium), non-toxic heavy metal (stannous and indium) and ammonium and low molecular weight substituted ammonium (mono-, di- and triethanolamine) salts; and (2) from about 100 I.U. to about 50,000 I.U. of a Vitamin D-like antirachitic compound.

Operable phosphonates of the above formula (I) include propane-1,2,3-triphosphonic acid; butane-1,2,3,4-tetraphosphonic acid; hexane-1,2,3,4,5,6-hexaphosphonic acid; hexane-1-hydroxy-2,3,4,5,6-pentaphosphonic acid; hexane-1,6-dihydroxy-2,3,4,5-tetraphosphonic acid; pentane-1,2,3,4,5-pentaphosphonic acid; heptane-1,2,3,4,5,6,7-heptaphosphonic acid; octane-1,2,3,4,5,6,7,8-octaphosphonic acid, nonane-1,2,3,4,5,6,7,8,9-nonaphosphonic acid; decane-1,2,3,4,5,6,7,8,9,10-decaphosphonic acid; and the pharmaceutically acceptable salts of these acids, e.g., sodium, potassium, calcium, magnesium, ammonium, triethanolammonium, diethanolammonium, and monoethanolammonium salts.

Propane-1,2,3-triphosphonic acid and salts thereof can be prepared by a process disclosed in U.S. Pat. No. 3,743,688, filed July 3, 1973.

Butane-1,2,3,4-tetraphosphonic acid and salts thereof can be prepared by a process disclosed in U.S. Pat. No. 3,755,504, filed Aug. 28, 1973.

The higher aliphatic vicinal phosphonates and salts thereof can be prepared by the process disclosed in U.S. Pat. No. 3,584,035 granted June 8, 1971.

Among the operable phosphonates encompassed by the above formula (II) are ethane-1-hydroxy-1,1-diphosphonic acid; methanediphosphonic acid; methanehydroxydiphosphonic acid; ethane-1,1,2-triphosphonic acid; propane-1,1,3,3-tetraphosphonic acid; ethane-2-phenyl-1,1-diphosphonic acid; ethane-2-naphthyl-1,1-diphosphonic acid; methanephenyldiphosphonic acid; ethane-1-amino-1,1-diphosphonic acid; methanedichlorodiphosphonic acid; nonane-5,5-diphosphonic acid; n-pentane-1,1-diphosphonic acid; methanedifluorodiphosphonic acid; methanedibromodiphosphonic acid; propane-2,2-diphosphonic acid; ethane-2-carboxy-1,1-diphosphonic acid; propane-1-hydroxy-1,1,3-triphosphonic acid; ethane-2-hydroxy-1,1,2-triphosphonic acid ethane-1-hydroxy-1,1,2-triphosphonic acid; propane-1,3-diphenyl-2,2-diphosphonic acid; nonane-1,1-diphosphonic acid; hexadecane-1,1-diphosphonic acid; pent-4-one-1-hydroxy-1,1-diphosphonic acid; octadec-9-ene-1-hydroxy-1,1-diphosphonic acid; 3-phenyl-1,1-diphosphono-prop-2-ene; octane-1,1-diphosphonic acid; dodecane-1,1-diphosphonic acid; phenylaminomethanediphosphonic acid; naphthylaminomethanediphosphonic acid; N,N-dimethylaminomethanediphosphonic acid; N-(2-dihydroxyethyl)-aminomethanediphosphonic acid; N-acetylaminomethanediphosphonic acid; aminomethanediphosphonic acid; dihydroxymethanediphosphonic acid; and the pharmaceutically acceptable salts of these acids, e.g., sodium potassium, calcium, magnesium, stannous, indium, ammonium, triethanolammonium, diethanolammonium, and monoethanoiammonium salts.

Mixtures of any of the foregoing phosphonic acids and/or salts can be used in the practice of this invention.

Ethane-1-hydroxy-1,1-diphosphonic acid, an especially preferred phosphonate, has the molecular formula $CH_3C(OH)(PO_3H_2)_2$. (According to nomenclature by radicals, the acid might also be named 1-hydroxyethylidene diphosphonic acid.)

While any pharmaceutically acceptable salt of ethane-1-hydroxy-1,1-diphosphonic acid can be used in the practice of this invention, the disodium dihydrogen salt is preferred. The other sodium, potassium, ammonium, and mono-, di-, and triethanolammonium salts and mixtures thereof are aslo suitable, provided caution is observed in regulating the total intake of cation species in the salt composition. These compounds can be prepared by any suitable method, however, an especially preferred method is disclosed in U.S. Pat. No. 3,400,149 granted Sept. 3, 1968.

Methanehydroxydiphosphonic acid and related compounds operable herein can be prepared, for example, by reaction of phosgene with an alkali metal dialkylphosphite. A complete description of these compounds and a method for preparing same is found in U.S. Pat. No. 3,422,137 granted Jan. 14, 1969.

Methanedihydroxydiphosphonic acid and salts useful herein and a method for preparing same are disclosed in U.S. Pat. No. 3,497,313 granted Feb. 24, 1970.

Methanediphosphonic acid and related compounds useful herein are described in detail in U.S. Pat. No. 3,213,030, granted Oct. 19, 1965. A preferred method of preparing such compounds is disclosed in U.S. Pat. No. 3,251,907 granted May 17, 1966.

Ethane-1,1,2-triphosphonic acid and related compounds which can be used in the compositions of this invention, as well as a method for their preparation, are fully described in U.S. Pat. No. 3,551,339 granted Dec. 29, 1970.

Propane-1,1,3,3-tetraphosphonic acid and related compounds useful herein, and a method for preparing same are fully disclosed in U.S. Pat. No. 3,400,176 granted Sept. 3, 1968. The higher methylene interrupted methylene phosphonate polymers can be prepared by the polymerization of ethylene-1,1-diphosphonic acid.

Pentane-2,2-diphosphonic acid and related compounds can be prepared in accordance with the method described by G. M. Kosolopoff in *J. Amer. Chem. Soc.*, 75, 1500 (1953).

Operable phosphonates of formula (III) above include the following:
Methanecyclobutylhydroxydiphosphonic acid
Methanecyclopentylhydroxydiphosphonic acid
Methanecyclohexylhydroxydiphosphonic acid
Methanecycloheptylhydroxydiphosphonic acid
Methanecyclooctylhydroxydiphosphonic acid
Methanecyclononylhydroxydiphosphonic acid
Methanecyclodecylhydroxydiphosphonic acid Each of the sodium, potassium, calcium, magnesium, stannous, indium, ammonium, monoethanolammonium, diethanolammonium and triethanolammonium salts of the above recited methanecycloalkylhydroxydiphosphonic acids as well as any other pharmaceutically acceptable salt of these acids, can be used in the practice of the present invention.

The phosphonates of formula (III) can be prepared by methods fully described in U.S. Pat. No. 3,584,125, granted June 8, 1971.

The preferred phosphonates of formula (IV) for the purpose of this invention are tris(phosphonomethyl)amine; tris(1-phosphonoethyl)amine; tris(2-phosphono-2-propyl)amine; and their pharmaceutically acceptable salts. Tris(phosphonomethyl)amine is especially preferred. The following are exemplary of compounds which can also be used.
(a) bis(phosphonomethyl)-1-phosphonoethyl amine;
(b) bis(phosphonomethyl)-2-phosphono-2-propyl amine;
(c) bis(1-phosphonoethyl)phosphonomethyl amine;
(d) bis(2-phosphono-2-propyl)phosphonomethyl amine;
(e) tris(1-phosphono-1-pentyl)amine;
(f) bis(phosphonomethyl)2-phosphono-2-hexyl amine; and
(g) the pharmaceutically acceptable salts of acids (a) through (f), e.g., sodium, potassium, calcium, magnesium, ammonium, triethanolammonium, diethanolammonium, and monoethanolammonium salts.

Mixtures of any of the foregoing tris(phosphonoalkyl)-amines and/or salts can also be used in the practice of this invention.

The tris(phosphonoalkyl)amines can be prepared, for example, by first preparing the corresponding ester in accordance with the general reaction:

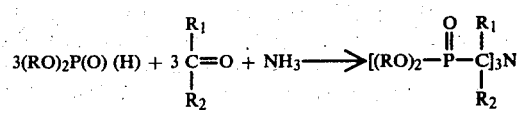

wherein R is alkyl and $R_1$ and $R_2$ are hydrogen or lower alkyl.

The free acids can be prepared by hydrolysis of the ester using strong mineral acids such as hydrochloric acid. The salts are, of course, prepared by neutralizing the acid with the base of the desired cation. The preparation of tris(phosphonoalkyl)amines is fully disclosed by Irani, et al., in Canadian Patent 753,207, issued Feb. 21, 1967.

The phosphonates of formula (V) include the following:
(1) 3,3,4,4,5,5-hexafluoro-1,2-diphosphonocyclopent-1-ene;
(2) 3,3,4,4-tetrafluoro-1,2-diphosphonocyclobut-1-ene; and
(3) 3,3,4,4,5,5,6,6-octafluoro-1,2-diphosphonocyclohex-1-ene.

The perfluorodiphosphonocycloalkenes can be prepared, for example, by reacting trialkyl phosphites with 1,2-dichloroperfluorocycloalk-1-enes in accordance with the procedures fully described by Frank in *J. Org. Chem.*, 31, #5, p. 1521.

The phosphonate of formula (VI) is referred to herein as cyclic tetraphosphonic acid. This compound and its pharmaceutically acceptable salts can be prepared by any suitable method, however, an especially preferred method is disclosed by Oscar T. Quimby, U.S. Pat. No. 3,387,024 granted June 4, 1968.

Operable phosphonates encompassed by the above formula (VII) are ethene-1,2-dicarboxy-1-phosphonic acid; and the pharmaceutically acceptable salts of these acids, e.g., sodium, potassium, calcium, magnesium, stannous, indium, ammonium, triethanolammonium, diethanolammonium, and monoethanolammonium salts. While the above formula (VII) is representative of cis-isomers, the corresponding trans-isomers are also useful herein. Reference hereinafter to ethene-1,2-dicarboxy-1-phosphonic acid or salts thereof, unless otherwise specified, is intended as contemplating the cis- and trans-isomers and mixtures thereof.

Ethene-1,2-dicarboxy-1-phosphonic acid and related compounds useful herein can be prepared by reaction of an ester of acetylenedicarboxylic acid and a dialkyl phosphite followed by hydrolysis and saponification. This method is more fully described in U.S. Pat. No. 3,584,124, granted June 8, 1971.

Operable carboxyphosphonates of the above formula (VIII) include ethane-1,2-dicarboxy-1,2-diphosphonic acid; ethane-1,2-dicarboxy-1,2-dihydroxy-1,2-diphosphonic acid; ethane-1,2-dicarboxy-1-hydroxy-1,2-diphosphonic acid; and the pharmaceutically acceptable salts of these acids, e.g., sodium, potassium, calcium, magnesium, ammonium, triethanolammonium, diethanolammonium, and monoethanolammonium salts.

Ethane-1,2-dicarboxy-1,2-diphosphonic acid, a preferred carboxyphosphonate herein, has the molecular formula $CH(COOH)(PO_3H_2)CH(COOH)(PO_3H_2)$. The most conveniently crystallizable salts of this acid are obtained when three, four or five of the acid hydrogens are replaced by sodium.

While any pharmaceutically acceptable salt of ethane-1,2-dicarboxy-1,2-diphosphonic acid can be used in the practice of this invention, the tetrasodium dihydrogen salt, the trisodium trihydrogen salt, the disodium tetrahydrogen salt, the monosodium pentahydrogen salt, and the mixtures thereof are preferred. The other sodium, potassium, ammonium, and mono-, di-, and triethanolammonium salts and mixtures thereof are also suitable, provided caution is observed in regulating the total intake of cation species in the salt composition.

Ethane-1,2-dicarboxy-1,2-diphosphonic acid and suitable salts thereof can be prepared in any convenient manner. For example, the reaction described by Pudovik in "Soviet Research on Organo-Phosphorus Compounds", 1949–1956, Part III, 547-85c. can be used to prepare the ester of ethane-1,2-dicarboxy-1,2-diphosphonic acid which in turn can, by ordinary hydrolysis reactions, be converted to the free acid form. Neutralization by alkali compounds such as sodium hydroxide, potassium hydroxide, carbonates and the like can be used to prepare a desired salt of the acid. A more detailed description of the preparation of these compounds is described in U.S. Pat. No. 3,562,166, granted Feb. 9, 1971.

Ethane-1,2-carboxy-1,2-dihydroxy-1,2-diphosphonic acid and related compounds useful herein can be prepared by reaction of an ester of ethane-1,2-dicarboxy-1,2-diphosphonic acid and an alkali metal hypohalite followed by hydrolysis and saponification. This method is more fully described in U.S. Pat. No. 3,579,570, granted May 18, 1971.

Phosphonates of formula (IX) can be prepared by a rearrangement reaction of a 2-haloethane-1-hydroxy-1,1-diphosphonic acid with about three equivalents of sodium hydroxide as described in U.S. Pat. No. 3,641,126.

The phosphonate of formula (X), ethylene-1,1-diphosphonic acid, can be prepared by the method of German Offen. No. 2,026,078.

Mixtures of any of the foregoing phosphonic acids and/or salts can be used in the practice of this invention.

The Vitamin D-like antirachitic compounds useful herein include activated ergosterol (Vitamin $D_2$ or calciferol), and activated 7-dehydrocholesterol (Vitamin $D_3$). These are available commercially or can be produced from their precursors (ergosterol and 7-dehydrocholesterol, respectively) by the application of energy to the molecule. The energy may be supplied by ultraviolet light, high speed electrons and the like. Thus, these precursors are themselves Vitamin D-like antirachitic compounds and can be administered and subsequently converted, in vivo, by sunlight to the D vitamins. While both Vitamins $D_2$ and $D_3$ are useful herein, Vitamin $D_3$ is preferred. These compounds and their properties are described in detail by H. R. Rosenberg, Chemistry and Physiology of the Vitamins, pp. 341–432 (1945).

In vivo, Vitamin D (i.e., Vitamins $D_2$ and $D_3$) is metabolized and a number of the metabolites thereof have been identified as the basis for the antirachitic activity associated with Vitamin D. The metabolites can, of course, be used in the practice of the present invention. Analogs of Vitamin D also exist and are similarly useful in the present invention. The Vitamin D-like antirachitic metabolites and analogs of Vitamin D include the following which are listed together with a reference disclosing how to synthesize or isolate them or a commercial source therefore and their activity in International Units (I.U.) per µg. The activity where indicated by an asterisk (*) is estimated.

TABLE I

| Name | Source | Activity |
|---|---|---|
| Vitamin $D_2$ | Widely Available | 40 |
| Vitamin $D_3$ | Widely Available | 40 |
| Dihydroxytachysterol$_2$ | Philips-Duphar (Netherlands) | 0.09 |
| Dihydrotachysterol$_3$ | Philips-Duphar (Netherlands) | 0.16 |
| 25-hydroxydihydrotachysterol$_3$ | U.S. Pat. No. 3,607,888 | 0.80 |
| 25-hydroxyergocalciferol | U.S. Pat. No. 3,585,221 | 60 |
| 25-hydroxycholecalciferol | Philips-Duphar (Netherlands) | 60 |
| 1α,25-dihydroxycholecalciferol | U.S. Pat. No. 3,697,559 | 20* |
| 5,6-trans-cholecalciferol | Biochemistry, Vol. 11, No. 14, pp. 2715–19 | 20* |
| 5,6-trans-25-hydroxycholecalciferol | Biochemistry, Vol. 11, No. 14, pp. 2715–19 | 20* |
| 24-nor-25-hydroxycholecalciferol | Biochemistry, Vol. 11, No. 14, pp. 2715–19 | 60* |
| 24-nor-5,6-trans-25-hydroxy-cholecalciferol | Biochemistry, Vol. 11, No. 14, pp. 2715–19 | 20–60* |
| 21,25-dihydroxycholecalciferol | Biochemistry, Vol. 9, No. 14, pp. 2917–22 | 10 - orally 20 - i.v. |
| 25,26-dihydroxycholecalciferol | Biochemistry, Vol. 9, No. 24, pp. 4776–80 | <4 |
| 24,25-dihydroxycholecalciferol | U.S. Pat. No. 3,715,374 | <10 - orally 20 - i.v. |
| 1α-hydroxycholecalciferol | Science, Vol. 180, No. 4082, pp. 190–91 | 20* |

The International Unit is defined in terms of the biological activity produced, as described more fully in U.S. Pharmacopiea, 15th revision, Mack Publishing Co. (1955). Strictly speaking, the I.U. is a fully accepted unit only for Vitamin D per se. The activity of Vitamin D-like antirachitic compounds is frequently referred to in the art in terms of the I.U. and since this measure of biological activity is the most nearly appropriate determinant of the levels of the Vitamin D-like compounds for use in the present invention, it is so used herein. The amount of the Vitamin D-like antirachitic compounds employed in the method of this invention must be sufficient to provide about 100 I.U. to about 50,000 I.U. per day. The preferred antirachitic compounds for use in the present invention are Vitamin $D_3$ and 1α-hydroxycholecalciferol which are well suited for oral administration.

The therapeutic dosage of phosphonate will vary with the particular condition being treated, the severity of the condition, and the duration of treatment; however, single dosages can range from 0.01 to 500 mg. per kilogram of body weight, preferably 0.1 to 50 mg./kg., with up to four dosages daily. The higher dosages within this range are, of course, required in the case of oral administration because of limited absorption. Repeated dosages greater than about 400 mg./kg. may produce toxic symptoms and should be avoided. Moreover, daily dosages greater than about 2000 mg./kg. (unless otherwise specified, the unit designated "mg./kg." as used herein refers to mg. of compound/kg. of body weight) are not requrired to produce the desired effect and may produce toxic side effects. Dosages of less than about 0.01 mg./kg. do not materially affect pathological demineralization, even administered intravenously. Table II below sets forth preferred dosages for various conditions which can be treated in accordance with this invention.

TABLE II

| Condition | Therapeutic Oral Dosage (mg./kg.) Up to Four Times/Day |
|---|---|
| Osteoporosis (post-menopausal)* | 0.25–25 |
| Osteoporosis (senile, et al.) | 0.25–25 |
| Paget's Disease | 1–50 |

*A larger initial dosage may be required, e.g., up to 500 mg./kg. followed by the specified dosage level.

The phosphonates can also be administered parenterally in aqueous solution by subcutaneous, intradermal, intramuscular, intraperitoneal, or intravenous injection. The preferred single dosage ranges by these modes of administration are as follows:

| | Therapeutic Dosage |
|---|---|
| Subcutaneous | 0.1–10 mg./kg. |
| Intradermal | 0.1–10 mg./kg. |
| Intramuscular | .05–5 mg./kg. |
| Intravenous | .05–5 mg./kg. |
| Intraperitoneal | .05–5 mg./kg. |

For purposes of oral administration (the preferred mode) the phosphonates can be in elixer form or formulated in unit dosage form, i.e., in the form of capsules, tablets or pills, together with the Vitamin D-like antirachitic compounds (especially Vitamin $D_3$) and a pharmaceutical carrier, each unit dosage form containing from 5 mg. to 10 g. of phosphonate and from about 100 to about 50,000 units of the antirachitic compound. The preferred concentration range of phosphonate in unit dosage forms intended for use by humans and smaller domesticated animals is from 10 mg. to 1000 mg., more preferably 50 mg. to 500 mg. and the preferred range of the antirachitic compounds is from 500 to about 50,000 International Units.

Representative compositions of the present invention are presented in the following examples.

Example I

Capsules are prepared by conventional methods, comprised as follows:

| Ingredient | mg per capsule |
|---|---|
| Disodium ethane-1-hydroxy-1,1-diphosphonate | 350.00 |
| Vitamin $D_3$ | 2000 I.U. |
| Starch | 55.60 |
| Sodium lauryl sulfate | 2.90 |

The above capsules administered orally twice daily substantially reduces bone decalcification in a patient weighing approximately 70 kilograms afflicted with osteoporosis. Similar results are attained when methanediphosphonic acid, methanedichlorodisphosphonic acid, methanehydroxydiphosphonic acid, ethane-1-amino-1,1-diphosphonic acid, phenylaminomethanediphosphonic acid, N,N-dimethylaminomethanediphosphonic acid, N-(2-hydroxyethyl)-aminomethanediphosphonic acid, N-acetylaminomethanediphosphonic acid, aminomethanediphosphonic acid, propane-1,2,3-triphosphonic acid, hexane-1,2,3,4,5,6-hexaphosphonic acid, and pent-4-ene-1-hydroxy-1,1-diphosphonic acid, respectively, are employed in the above described capsule in place of disodium ethane-1-hydroxy-1,1-diphosphonate. Comparable results are secured when the Vitamin $D_2$ is used in place of Vitamin $D_3$ in the above capsules in that no mineralization defects are observed.

EXAMPLE II

Tablets are prepared by conventional methods, formulated as follows:

| Ingredient | mg per tablet |
|---|---|
| Methanediphosphonic acid | 125.00 |
| Vitamin $D_2$ | 750 I.U. |
| Lactose | 40.00 |
| Starch | 2.50 |
| Magnesium stearate | 1.00 |

When administered orally four times daily, the above composition significantly reduces bone loss in a patient weighing approximately 50 kilograms suffering from Paget's disease.

Similar results are achieved with tablets formulated as above but replacing methanediphosphonic acid with the disodium salt of ethane-1-hydroxy-1,1-diphosphonic acid, the trisodium salt of methanediphosphonic acid, the disodium salt of methanehydroxydiphosphonic acid, aminomethanediphosphonic acid, the monocalcium salt of methanedichlorodiphosphonic acid, methylaminomethanediphosphonic acid, propane-1,2,3-triphosphonic acid; the pentasodium salt of butane-1,2,3,4-tetraphosphonic acid, the monoindium salt of octadec-9-ene-1-hydroxy-1,1-diphosphoric acid, the monostannous salt of hexadecane-1,1-diphosphonic acid, and propane-1,1-diphosphonic acid, respectively.

The lactose employed in this example is replaced by sucrose and the magnesium stearate by sodium carboxymethylcellulose without affecting the desired properties of the tablet.

Additional tablet compositions are prepared in accordance with the invention as follows:

| Ingredient | Ex. | Mg per Tablet | | | | | | |
|---|---|---|---|---|---|---|---|---|
| | | III | IV | V | VI | VII | VIII | IX |
| Cyclohexylhydroxymethane-diphosphonic acid | | 80.0 | | | | | | |
| Tris(phosphonomethyl)amine | | | 100.0 | | | | | |
| 3,3,4,4,5,5-hexafluoro-1,2-diphosphonocyclopent-1-ene | | | | 120.0 | | | | |
| Cyclic tetraphosphonic acid | | | | | 50.0 | | | |
| Ethene-1,2-dicarboxy-1-phosphonic acid | | | | | | 85.0 | | 40.0 |
| Ethane-1,2-dicarboxy-1,2-diphosphonic acid | | | | | | | 30.0 | 15.0 |
| Vitamin D$_3$ (International Units) | | 750 | 1000 | 5000 | 500 | 2000 | 3000 | 3000 |
| Lactose | | 97.0 | 31.0 | 31.0 | 73.0 | 97.0 | 30.0 | 97.0 |
| Starch | | 45.0 | 13.0 | 13.0 | 57.0 | 45.0 | | 45.0 |
| Stearic acid | | | | | 6.0 | | | 6.0 |
| Talc | | 35.5 | 6.5 | 6.5 | 9.0 | 35.0 | 5.0 | 9.0 |
| Calcium stearate | | | 1.0 | 1.0 | | | 1.0 | |
| Ethyl cellulose | | | 16.0 | 16.0 | | | 15.0 | |

Each of the above tablets are used in the treatment of a 90 kg. patient suffering from idiopathic osteoporosis. Bone loss is substantially reduced and no adverse symptoms are observed when these tablets are administered in a number sufficient to provide a daily dosage of phosphonate of approximately 450 mg.

EXAMPLES X TO XXVI

Tablets are formulated as in Example VIII except that disodium ethane-1-hydroxy-1,1-disphosphonate replaces the ethane-1-hydroxy-1,1-diphosphonic acid and 3000 International Units of the following Vitamin D-like antirachitic compounds are used:

| EXAMPLE | COMPOUND |
|---|---|
| X | Vitamin D$_2$ |
| XI | Vitamin D$_3$ |
| XII | Dihydroxytachysterol$_2$ |
| XIII | Dihydrotachysterol$_3$ |
| XIV | 25-hydroxydihydrotachysterol$_3$ |
| XV | 25-hydroxyergocalciferol |
| XVI | 25-hydroxycholecalciferol |
| XVII | 1α,25-dihydroxycholecalciferol |
| XVIII | 5,6-trans-cholecalciferol |
| XIX | 5,6-trans-25-hydroxycholecalciferol |
| XX | 24-nor-25-hydroxycholecalciferol |
| XXI | 24-nor-5,6-trans-25-hydroxycholecalciferol |
| XXII | 21,25-dihydroxycholecalciferol |
| XXIII | 25,26-dihydroxycholecalciferol |
| XXIV | 24,25-dihydroxycholecalciferol |
| XXV | 1α-hydroxycholecalciferol |
| XXVI | Vitamin D$_3$(1500 units) and 2α-hydroxycholecalciferol (1500 units) |

The above tablets are administered to a 70 Kg. patient suffering from Paget's disease in a number sufficient to provide a daily dosage of about 500 mg. of phosphonate. Bone loss is substantially reduced and no adverse symptoms are observed.

Similar results are obtained when the above tablets are administered to a 70 Kg. patient suffering from osteoporosis in a number sufficient to provide a daily dosage of about 250 mg. of phosphonate.

What is claimed is:

1. A method of treating Paget's disease comprising conjointly administering to an animal afflicted therewith therapeutic dosages of a phosphonate selected from the group consisting of:

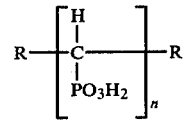

I.

wherein each p is hydrogen or CH$_2$OH and n is an integer of from 3 to 10:

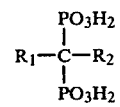

II.

wherein R$_1$ is hydrogen, alkyl containing from 1 to about 20 carbon atoms, alkenyl containing from 2 to about 20 carbon atoms, phenylethenyl, benzyl, halogen, hydroxyl, amino, dimethylamino, diethylamino, —CH$_2$COOH, —CH$_2$PO$_3$H$_2$, CH(PO$_3$H$_2$)(OH), or —[CH$_2$C(PO$_3$H$_2$)$_2$]$_n$H wherein n is 1 to 15, R$_2$ is hydrogen, lower alkyl, amino, benzyl, halogen, hydroxyl, —CH$_2$COOH, —CH$_2$PO$_3$H$_2$, or —CH$_2$CH$_2$PO$_3$H$_2$;

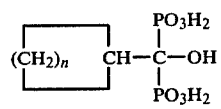

III.

wherein n is an integer of from 3 to 9;

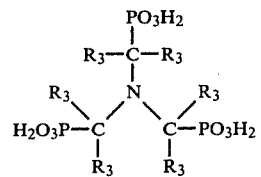

IV.

wherein each R$_3$ is hydrogen or lower alkyl;

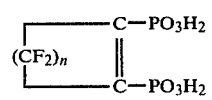

V.

wherein n is an integer of from 2 to 4;

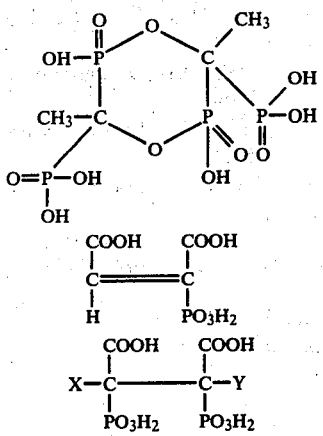

VI.

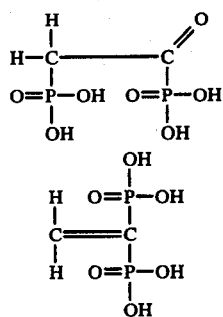

VII.

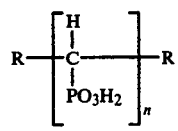

VIII.

wherein X and Y are each hydrogen or hydroxy;

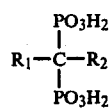

IX.

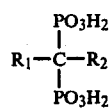

X.

and the pharmaceutically acceptable salts thereof; and (2) from about 100 I.U. to about 50,000 I.U. of a Vitamin-D active antirachitic compound.

2. A method of treating osteoporosis comprising conjointly administering to an aminal afflicted therewith therapeutic dosages of a phosphonate selected from the group consisting of:

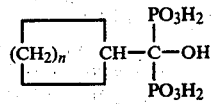

I.

wherein each P is hydrogen or CH₂CH and n is an integer of from 3 to 10:

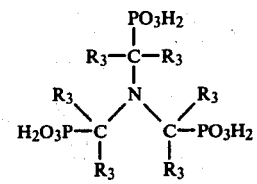

II.

wherein $R_1$ is hydrogen, alkyl containing from 1 to about 20 carbon atoms, alkenyl containing from 2 to about 20 carbon atoms, phenylethenyl, benzyl, halogen, hydroxyl, amino, dimethylamino, diethylamino, —CH₂COOH, —CH₂PO₃H₂, CH(PO₃H₂)(OH), or —[CH₂C(PO₃H₂)₂]ₙH wherein n is 1 to 15, $R_2$ is hydrogen, lower alkyl, amino, benzyl, halogen, hydroxyl, —CH₂COOH, —CH₂PO₃H₂, or —CH₂CH₂PO₃H₂;

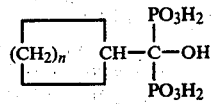

III.

wherein n is an integer of from 3 to 9:

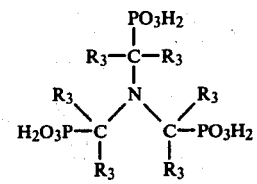

IV.

wherein each $P_3$ is hydrogen or lower alkyl;

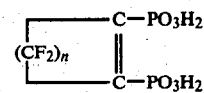

V.

wherein n is an integer of from 2 to 4;

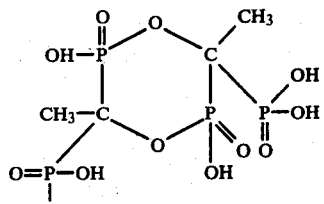

VI.

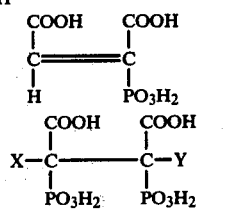

VII.

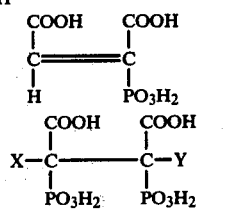

VIII.

wherein X and Y are each hydrogen or hydroxy;

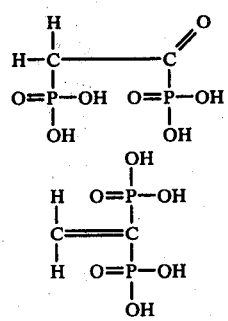

IX.

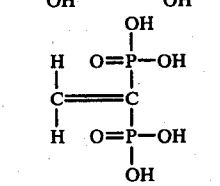

X.

and the pharmaceutically acceptable salts thereof, and (2) from about 100 I.U. to about 50,000 I.U. of a Vitamin-D active antirachitic compound.

3. The method of claim 1 or 2 wherein the phosphonate is ethane-1-hydroxy-1,1-diphosphonic acid or a pharmaceutically acceptable salt thereof.

4. The method of claim 1 or 2 wherein the phosphonate is dichloromethanediphosphonic acid or a pharmaceutically acceptable salt thereof.

5. The method of claim 1 or 2 wherein the phosphonate is tris(phosphonomethyl)amine or a pharmaceutically acceptable salt thereof.

6. The method of claim 1 or 2 wherein the phosphonate is methanecyclohexylhydroxydiphosphonic acid or a pharmaceutically acceptable salt thereof.

7. The method of claim 1 or 2 wherein the phosphonate is 3,3,4,4,5,5-hexafluoro-1,2-diphosphonocyclopent-1-ene or a pharmaceutically acceptable salt thereof.

8. The method of claim 1 or 2 wherein the phosphonate is cyclic tetraphosphonic acid or a pharmaceutically acceptable salt thereof.

9. The method of claim 1 or 2 wherein the phosphonate is ethene-1,2-dicarboxy-1-phosphonic acid or a pharmaceutically acceptable salt thereof.

10. The method of claim 1 or 2 wherein the phosphonate is ethane-1,2-dicarboxy-1,2-diphosphonic acid or a pharmaceutically acceptable salt thereof.

11. The method of claim 1 or 2 wherein the Vitamin D-active antirachitic compound is selected from the group consisting of Vitamin $D_2$; Vitamin $D_3$; dihyrdoxytachysterol$_2$; dihydrotachysterol$_3$; 25-hydroxydihydrotachysterol$_3$; 25-hydroxyergocalciferol; 25-hydroxycholecalciferol; 1α,25-dihydroxycholecalciferol; 5,6-trans-cholecalciferol; 5,6-trans-25-hydroxycholecalciferol; 24-nor-25-hydroxycholecalciferol; 24-nor-5,6-trans-25-hydroxycholecalciferol; 21,25-dihydroxycholecalciferol; 25,26-dihydroxycholecalciferol; 24,25-dihydroxycholecalciferol; 1α-hydroxycholecalciferol; and mixtures thereof.

12. The method of claim 1 or 2 wherein the antirachitic compound is Vitamin $D_3$.

13. The method of claim 3 wherein the antirachitic compound is Vitamin $D_3$.

14. The method of claim 4 wherein the antirachitic compound is Vitamin $D_3$.

15. The method of claim 1 or 2 wherein the antirachitic compound is 1α-hydroxycholecalciferol.

16. The method of claim 3 wherein the antirachitic compound is 1α-hydroxycholecalciferol.

17. The method of claim 4 wherein the antirachitic compound is 1α-hydroxycholecalciferol.

18. The method of claim 5 wherein the antirachitic compound is 1α-hydroxycholecalciferol.

19. The method of claim 1 or 2 wherein the Vitamin-D active antirachitic compound is Vitamin $D_2$.

20. The method of claim 3 wherein the Vitamin-D active antirachitic compound is Vitamin $D_2$.

21. The method of claim 4 wherein the Vitamin-D active antirachitic compound is Vitamin $D_2$.

* * * * *